United States Patent [19]

Boussignac et al.

[11] Patent Number: 5,036,847
[45] Date of Patent: Aug. 6, 1991

[54] BREATHING AID

[76] Inventors: Georges Boussignac, 1 Allée de Provence; Jean-Claude Labrune, 2 Avenue de Guyenne, both of 92160 Antony, France

[21] Appl. No.: 576,461
[22] PCT Filed: Mar. 29, 1990
[86] PCT No.: PCT/FR90/00214
§ 371 Date: Sep. 18, 1990
§ 102(e) Date: Sep. 18, 1990
[87] PCT Pub. No.: WO90/11792
PCT Pub. Date: Oct. 18, 1990

[30] Foreign Application Priority Data
Mar. 31, 1989 [FR] France ............... 89 04280

[51] Int. Cl.5 .................................... A61M 16/04
[52] U.S. Cl. ...................... 128/207.14; 128/203.12; 128/203.25; 128/205.25
[58] Field of Search .............. 128/207.14, 207.15, 128/207.16, 911, 912, 204.18, 204.25, 205.25, 206.21, 204.24, 205.19, 203.12, 203.25, 205.11; 604/101, 102

[56] References Cited

U.S. PATENT DOCUMENTS

| | | | |
|---|---|---|---|
| 2,791,217 | 5/1955 | Iskander | 128/203 |
| 3,859,995 | 1/1975 | Colston | 128/204.25 |
| 3,881,479 | 5/1975 | Carden | 128/145.8 |
| 3,915,173 | 10/1975 | Brekke | 128/351 |
| 4,265,237 | 5/1981 | Schwanbom et al. | 128/204.25 |
| 4,270,530 | 6/1981 | Baum et al. | 128/204.25 |
| 4,520,812 | 6/1985 | Freitag et al. | 128/207.14 |
| 4,573,462 | 3/1986 | Baum | 128/204.25 |
| 4,584,998 | 4/1986 | McGrail | 128/207.15 |
| 4,612,929 | 9/1986 | Schubert et al. | 128/204.25 |
| 4,739,756 | 4/1988 | Horn | 128/207.14 |
| 4,751,924 | 6/1988 | Hammerschmidt et al. | 128/207.15 |

FOREIGN PATENT DOCUMENTS

| | | |
|---|---|---|
| 0112668 | 7/1984 | European Pat. Off. . |
| 0153991 | 9/1985 | European Pat. Off. . |
| 0245142 | 11/1987 | European Pat. Off. . |
| 160709 | 6/1903 | Fed. Rep. of Germany . |
| 2613639 | 10/1988 | France . |
| 2057273 | 1/1981 | United Kingdom . |

OTHER PUBLICATIONS

Trang et al., Intensive Care Medicine, 13(6), No. 65, 1987 (Abstract).
Trang et al., Intensive Care Medicine, 13(6), No. 100, 1987 (Abstract).
Boussignac et al., Neonatal Respiration, No. 1150, (Abstract).
Mion et al., ASA Congress in San Francisco, Oct., 1988 (Abstract).
Isabey et al., Mechanics of Breathing II: Airways, Abstract No. 1129.
Isabey et al., "Effect of Air Entrainment on Airway Pressure During Endotracheal Gas Injection," presented in part at the 71st annual mtg. of the FASEB in Washington, D.C., 3/29–4/2/87.

Primary Examiner—Edgar S. Burr
Assistant Examiner—Stephen R. Funk
Attorney, Agent, or Firm—Fisher, Christen & Sabol

[57] ABSTRACT

Breathing aid comprising a tube (4) which forms a main channel (5) and which is intended to be connected by its distal end (3) to a breathing tract of a patient so that the main channel (5) connects the breathing system of the patient to the outside. The breathing aid further comprising at least one auxiliary channel (8,8.1) for injecting a gas jet for ventilating the patient and opening into the main channel (5) close to the distal end (7) thereof. According to the invention this device is characterized in that at least the distal end of the auxiliary channel (8,8.1) opening into the main channel (5) is parallel thereto and in that, opposite the distal orifice (17) of the auxiliary channel (8,8.1), a face (14b) is provided for deflecting the breathable ventilation gas jet towards the inside of said main channel (5).

12 Claims, 3 Drawing Sheets

BREATHING AID

BACKGROUND OF THE INVENTION

1. Field of the Invention

The present invention relates to a breathing aid which can be used on patients whose spontaneous respiration is absent or insufficient, whether they are under artificial respiration or not.

2. Description of Related Art

Different devices are known, such as masks, probes or oral, nasal, endotracheal, tracheotomic cannulae for providing the junction between the artificial respiration and/or anaesthetic appliance and the breathing system of a patient. Such devices, essentially in the form of tubes, depending on the case, may comprise immobilization means such as lugs or collars close to the proximal end for maintaining them on the mouth or nose of the patient, or else inflatable balloons close to the distal end for maintaining them in the trachea by friction.

Known devices have considerable drawbacks. Thus, for example, when a tube of known type is disconnected from the artificial breathing device and when the patient requires oxygen enriched air, it is necessary to introduce into said tube a probe connected to a source of oxygen. Furthermore, in the case of insufficient spontaneous respiration, the patient must necessarily remain connected to the breathing appliance until his spontaneous respiration is completely restored.

Thus, to overcome such drawbacks, breathing aids have already been proposed which, in addition to the main channel formed by the tube, comprise at least an auxiliary channel, formed for example in the wall of said tube, for injecting a breathable gas jet (oxygen, air or air-oxygen mixture) for ventilating the patient, this auxiliary channel opening into the main channel close to the distal end thereof.

However, such breathing aids with auxiliary breathable gas injection channels have the major drawback that said breathable gas jet strikes the mucous membrane directly, so that it is traumatized.

SUMMARY OF THE INVENTION

The main object of the present invention is to overcome this drawback. For this, according to the invention, the breathing aid comprising a tube which forms the main channel and which is intended to be connected by its distal end to a breathing tract of a patient so that said main channel connects the breathing system of said patient to the outside, said device comprising in addition at least one auxiliary channel for injecting a breathable gas jet for ventilating said patient and opening into said main channel close to the distal end thereof, is remarkable in that at least the distal end of said auxiliary channel opening into the main channel is parallel thereto and in that, opposite the distal orifice of said auxiliary channel, means are provided for deflecting said breathable ventilation gas jet towards the inside of said main channel.

Thus, the pressurized breathable gas jet passing through said auxiliary channel is deflected towards the axis of the main channel, when it penetrates therein. Downstream of said deflection means, i.e. inside the main channel, the pressure of said breathable gas jet drops and the jet leaves at low pressure through the distal orifice of the tube. Experience shows that downstream of the distal outlet of the tube, the pressure is low and kept constant in the whole breathing space. This pressure depends on the breathable gas flow in the auxiliary channels.

Consequently, with the breathing aid in accordance with the invention, it is for example possible to supply oxygen and an air-oxygen mixture directly into the lungs, at the height of the carina and thus eliminate the dead space which exists in present day probes and which is about a third of the total breathing volume for an adult and about half for premature newly-born children.

Elimination of this dead space corresponds to an increase in performance of the breathing cycle of more than 25% in all cases of patients and close to 50% in some cases.

In the case where said auxiliary channel is formed in the wall of said tube, it is advantageous for said distal orifice of said auxiliary channel to be formed in a first face diverging from said main channel, and for said deflection means to be formed in a second slanting face disposed opposite said first face and converging in the direction of the distal orifice of said main channel.

In addition, when several auxiliary channels are formed in the wall of said tube, it is preferable for the distal orifices of said auxiliary channels to be formed in the first annular face widening said main channel and for said deflection means to be formed by a second annular face, disposed opposite said first face and converging in the direction of the distal orifice of said main channel.

Downstream of said second face, between it and the distal orifice of the main channel, the latter may be cylindrical. However, experience has shown that it is preferable for the end portion of the main channel to be slightly widened. In addition, according to another feature of the invention, said second face is extended towards said orifice of the main channel by a wall widening said main channel slightly.

The deflection means may be formed directly in the internal wall of said tube. However, for ease of manufacture, it is advantageous for said deflection means to be formed on an end-piece fixed to the distal end of said tube.

When the device of the invention comprises a plurality of auxiliary channels, it is advantageous for at least some of them to be supplied in common with breathable gas. Such a common supply for said channels may be provided via a distribution ring, coaxial with said tube. Moreover, said auxiliary channels not supplied in common may serve for introducing additional gas products, such as medicinal products or humidity.

To be able to obtain a double flow device for promoting breathing out as well as breathing in of a patient, the device according to the invention may comprise at least one additional auxiliary channel, independent of said auxiliary channel and connected to a pressurized gas source, said additional auxiliary channel opening into said main channel close to the proximal end thereof, and at least the proximal end of said additional auxiliary channel opening into the main channel is parallel thereto, whereas, opposite the proximal orifice of said additional auxiliary channel, means are provided for deflecting the gas jet passing through the latter in the direction of the inside of said main channel.

Preferably, in this latter embodiment, the proximal part of the device is similar if not identical to the distal portion of said device, at least in so far as the arrangement of said auxiliary channels and said deflection means is concerned.

Thus, it can be seen that the device according to the invention makes possible:

intubation of the breathing aid without stopping, injection of medicaments, anaesthetics or humidity during the breathing assistance, dynamic measurement of the pressures, for it is sufficient to provide auxiliary channels in which appropriate probes are disposed, increase of the exchange volume, for the pressure is self-limited and there is no risk of crushing the pulmonary capillaries, reduction, for the same amount of oxygen exchanged, of the proportion of oxygen in the mixture, which reduces correspondingly the secondary effects of the assistance, the possibility of using less costly breathing devices than the present ones.

The breathing aid according to the invention makes it possible to use the minimum pressure differential required rhus bringing a maximum volume of breathing fluid.

Furthermore, the physical configuration of the device of the invention makes it possible to keep a sufficient inner diameter to permit the passage of instruments and medical probes which the operator desires to use.

BRIEF DESCRIPTION OF THE DRAWINGS

The figures of the accompanying drawings will better show how the invention may be put into practice. In these figures, identical references designate similar elements.

DETAILED DESCRIPTION OF THE PREFERRED EMBODIMENTS

Figure 1:
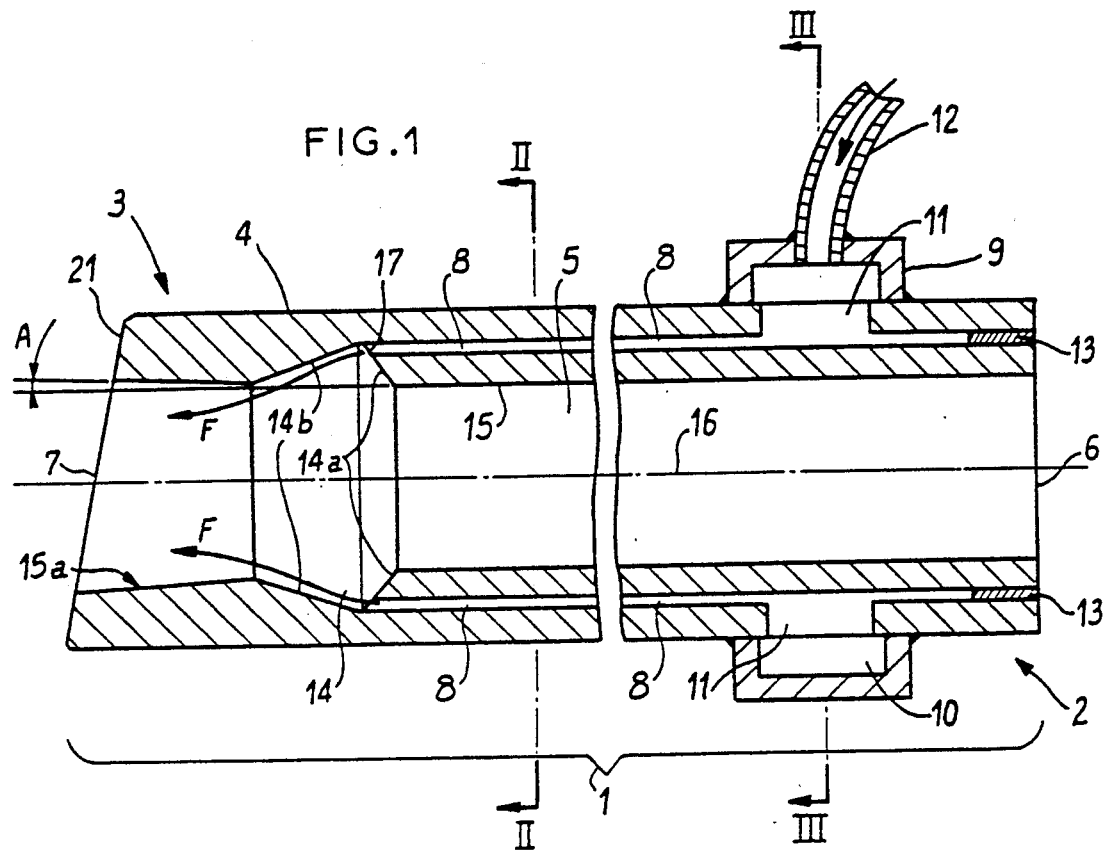
FIG. 1 is a schematic and partial view, in enlarged axial section, of a first embodiment of the device of the invention.

In FIG. 1, only the proximal 2 and distal 3 ends of an embodiment 1 of the device of the invention have been shown schematically and on a larger scale. This embodiment may form, for example, an endotracheal oro-nasal probe with or without balloon, an endotracheal pediatric probe, a gas monitoring probe, an endobronchial probe, a naso-pharyngeal probe, an anatomic intubation probe for children, a neo-natal Cole probe, a Guedel cannula probe or a nasal oxygenotherapy probe.

The device 1 comprises a tube 4, flexible or preformed (to be adapted to the morphology of the patient) defining a main channel 5 opening, through orifice 6, at the proximal end 2 and, through orifice 7, at the distal end 3.

Thus, the main channel 5 is capable of providing the passage between orifices 6 and 7, one (orifice 7) of which is intended to be located inside the breathing tracts of a patient and the other (orifice 6) is intended to be located outside said patient. This orifice 6 may open to the free air and, in this case, the patient may breathe in fresh air and breathe used air out through the main channel 5. Orifice 6 may also be connected to a pressurized breathable gas source (not shown) and a unidirectional valve system may be provided so that the patient breathes in the breathable gas from said source through said main channel 5 and breathes the used gas out to the free air, also through this main channel.

The diameter of main channel 5 is a few millimeters. Satisfactory tests have been carried out with diameters of 3 mm, 7 mm and 8 mm.

Furthermore, in the thickness of the wall of tube 4 are formed auxiliary channels 8 extending over almost the whole of the length of the main channel 5. These auxiliary channels 8 are intended to be connected to a pressurized breathable gas source (not shown). For example, this pressure is a few bars (1,2 or 4 bars) and it is adjustable.

Figure 3:
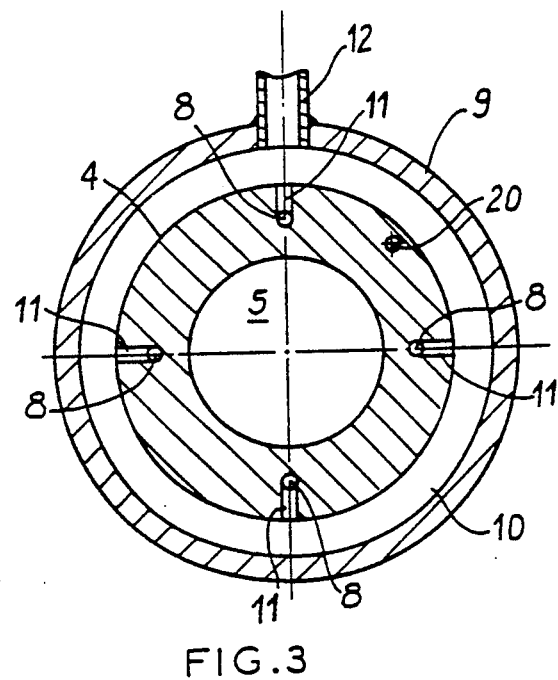

As is shown in FIGS. 1 and 3, connection to the pressurized breathable gas source may be provided by means of a ring 9, sealingly surrounding tube 4, on the proximal end 2 side and defining a sealed annular chamber 10 about said tube. The auxiliary channels 8 are placed in communication with chamber 10 through local cut-outs 11 of the wall of tube 4 and said chamber 10 is connected to said breathable gas source by a connection 12. Of course, the proximal ends of the channels 8 are closed, for example by plugs 13.

The auxiliary channels 8 have a smaller diameter than that of the main channel 5. The diameter of the auxiliary channels 8 is preferably less than 1 mm and, advantageously, is about 400 to 800 microns. On the distal side, the auxiliary channels 8 open into a recess 14 in the inner wall 15 of tube 4. Recess 14 is annular and centered on axis 16 of the distal end 3. It comprises a face 14a, substantially transversal or slightly slanting so as to form a widening of the main channel 5, into which said auxiliary channels open through their orifices 17, as well as a face 14b following face 14a and converging in the direction of axis 16.

Preferably, between the convergent slanting face 14b and the distal orifice 7, the internal wall 15 has a portion 15a widening slightly outwardly, as is illustrated by angle A in FIG. 1.

Thus, when the auxiliary channels 8 are supplied with pressurized breathable gas through elements 9 to 12, the corresponding gas jets strike the slanting face 14b, which deflects them in the direction of axis 16 (arrows F in FIG. 1) generating close thereto a zone of depression promoting the gas flow inside the main channel 5, from the proximal orifice to the distal orifice. Thus, breathing in of the patient is promoted.

Preferably, the distance between each of orifices 17 and orifice 7 is about 1 to 2 cm.

Downstream of orifice 7, the pressure in the pulmonary cavity is low and practically constant.

Thus, with the invention, breathing assistance is obtained which is not aggressive for the patient, with practically total disappearance of the dead space inherent in known probes.

Figure 4:
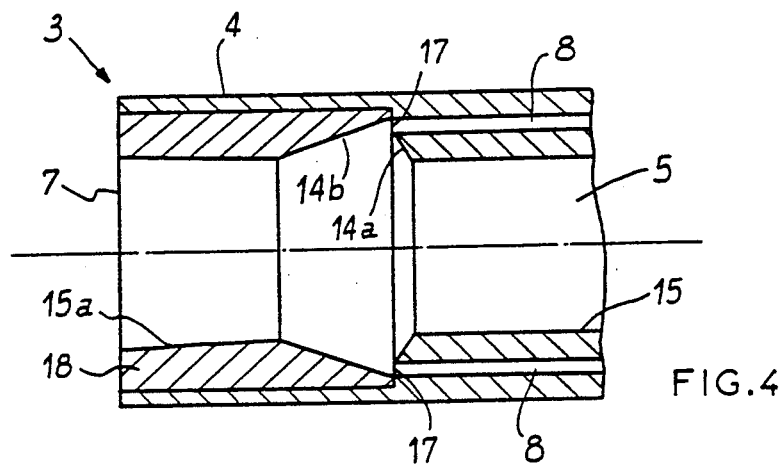
Figure 5:
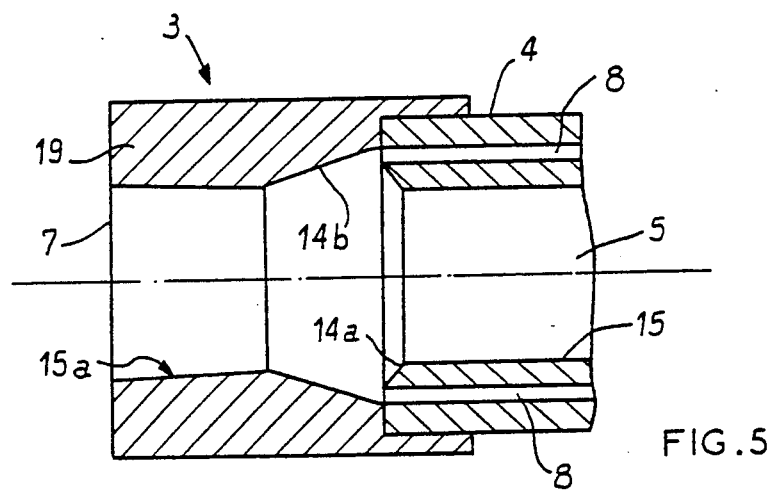

In the embodiment of the invention illustrated in FIG. 1, it has been shown that the assembly of faces 14a and 14b was formed by recessing the internal wall 15 of main channel 5. It goes without saying that this operating mode is not limitative and that faces 14a and 14b may be obtained in different ways. For example, in FIGS. 4 and 5, face 14a is formed in the internal wall 15 of tube 4 whereas face 14b is provided on an end-piece 18 or 19 fitting into (end-piece 18) or outside (end-piece 19) tube 4.

Of course, in this case, orifice 7 and the divergent wall 15a are carried by the corresponding end-piece 18 or 19.

Figure 2:
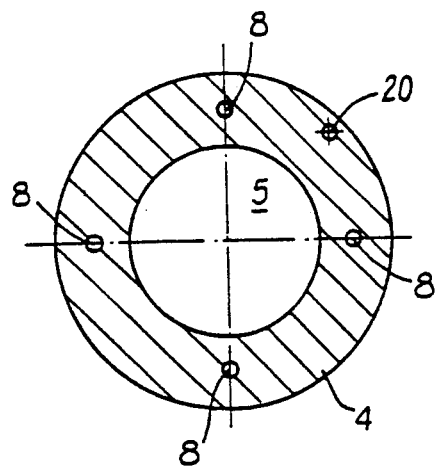
FIGS. 2 and 3 are cross-sections, respectively through lines II—II and III—III of FIG. 1, FIGS. 4 and 5 illustrate, schematically in enlarged axial section, two variants for the distal end of the device of the invention.

As shown in FIGS. 2 and 3, the auxiliary channels 8 are spaced evenly about the axis of tube 4. Their number is variable depending on the uses (adult or child), but it is generally between three and nine.

It will be noted that at least one of the auxiliary channels 8 instead of being connected in common with the others to the pressurized breathable gas source (via elements 9 to 12) may be continually supplied from the breathable gas source, so as to maintain a positive pressure in the lungs of the patient during or at the end of the breathing out phase caused by blowing gas into the auxiliary channels 8 (anti collapse effect).

According to another variant of the invention, one of the auxiliary channels 8 may also be specialized for supplying a medical fluid or humidification fluid, if the pressurized source does not have the required characteristics.

To provide humidification, the auxiliary channel bringing water (warm) is preferably curved in a U at its distal end, and opens into a cavity formed in the internal wall 15, into which cavity also emerges a channel bringing the pressurized air. In said cavity, situated preferably between recess 14 and the distal orifice 7, the water channel and the air channel open facing each other, namely substantially on the same axis, the two fluids (air and water) arriving in opposite directions, which permits vaporization of the water, the vapor obtained being then entrained by the blown air.

At least one additional channel 20 may be provided in the thickness of tube 4 so as to open into the distal end face 21 of tube 4 and serve for housing a pressure measurement device (not shown).

When at least two pressure tappings are present, particularly at each of the ends of the tube, through the difference of the measured pressures the gas flow can be calculated.

Tube 4 may comprise at distal end 3 an inflatable balloon (not shown) having necessary safety devices or any other balloon behaving as a safety valve in the case of an overpressure in the lungs. This balloon may be inflated from an additional channel (not shown) associated with tube 4.

A safety device may be formed simply by a resilient sleeve surrounding the tube, partially bonded thereto, and overlapping a perforation formed through the wall of said tube, particularly close to the proximal end. Thus, when the internal pressure becomes too high, the gas may flow through said perforation and then between the external wall of the tube and the internal wall of the resilient sleeve. If a safety sleeve is also provided in the vicinity of the distal end, the corresponding perforation, being placed beyond a possible friction holding balloon, must place the inside of the tube in communication with the ambient air; said balloon must then be circumvented, which is obtained for example by placing it about the resilient sleeve.

Figure 6:
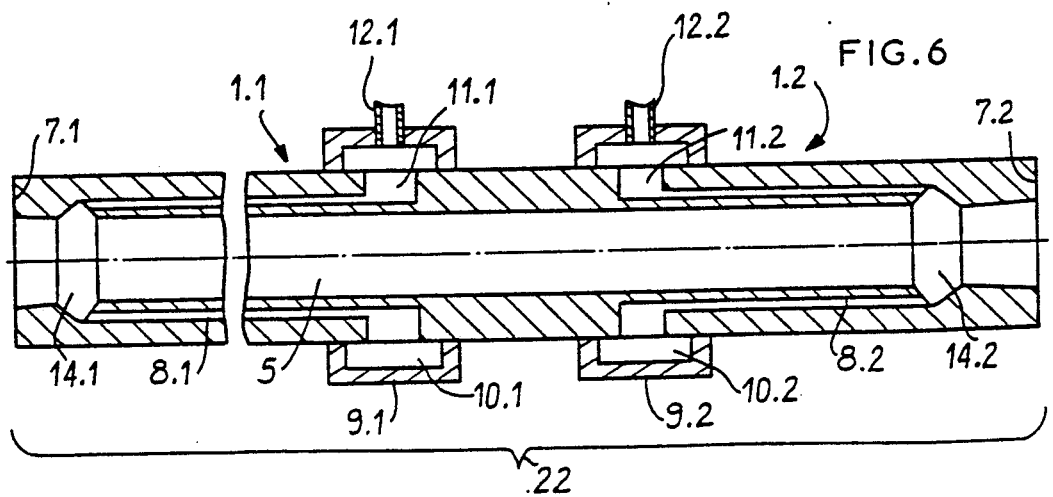
FIG. 6 shows, in schematic and partial axial section, a double flow variant of the device according to the invention.

The embodiment 22 of the device of the invention, shown in FIG. 6, comprises two devices 1.1 and 1.2, each of a structure similar to that (1) of FIG. 1, joined together by their orifices 6, device 1.2 being possibly shorter than device 1.1. In this embodiment 22, the distal orifice (inside the patient) is formed by orifice 7.1 of device 1.1 whereas the proximal orifice (outside the patient) is formed by orifice 7.2 of device 1.2. Each of the devices 1.1 and 1.2 is provided with a pressurized breathable gas system 9.1 to 12.1 and 9.2 to 12.2, supplying respective channels 8.1 or 8.2 opening into annular recesses 14.1 or 14.2 respectively close to said orifices 7.1 and 7.2. Device 22 forms a double flow probe. With this device positioned on the patient (i.e. device 1.1 being at least partially introduced into a breathing tract of the patient whereas device 1.2 and rings 12.1 and 12.2 are outside said patient), channels 8.1 (through elements 9.1 to 12.1) and channels 8.2 (through elements 9.2 to 12.2) are supplied alternately with pressurized breathable gas, so as to promote alternate breathing in and breathing out of the patient.

For this, a device (not shown) for switching and adjusting the flowrates and the gas blowing times is connected to rings 9.1 and 9.2 on the one hand and to the gas source on the other.

The breathing tube thus formed permits breathing assistance with blowing and breathing assistance with expiration, provided that a continuous flow is provided ensuring the safety and limiting the risk of pulmonary collapse.

The pressure in channels 8.2 is advantageously higher than the pressure in channels 8.1, for the entrainment effect of the fluid contained in the probe is not of the same kind.

Figure 7:
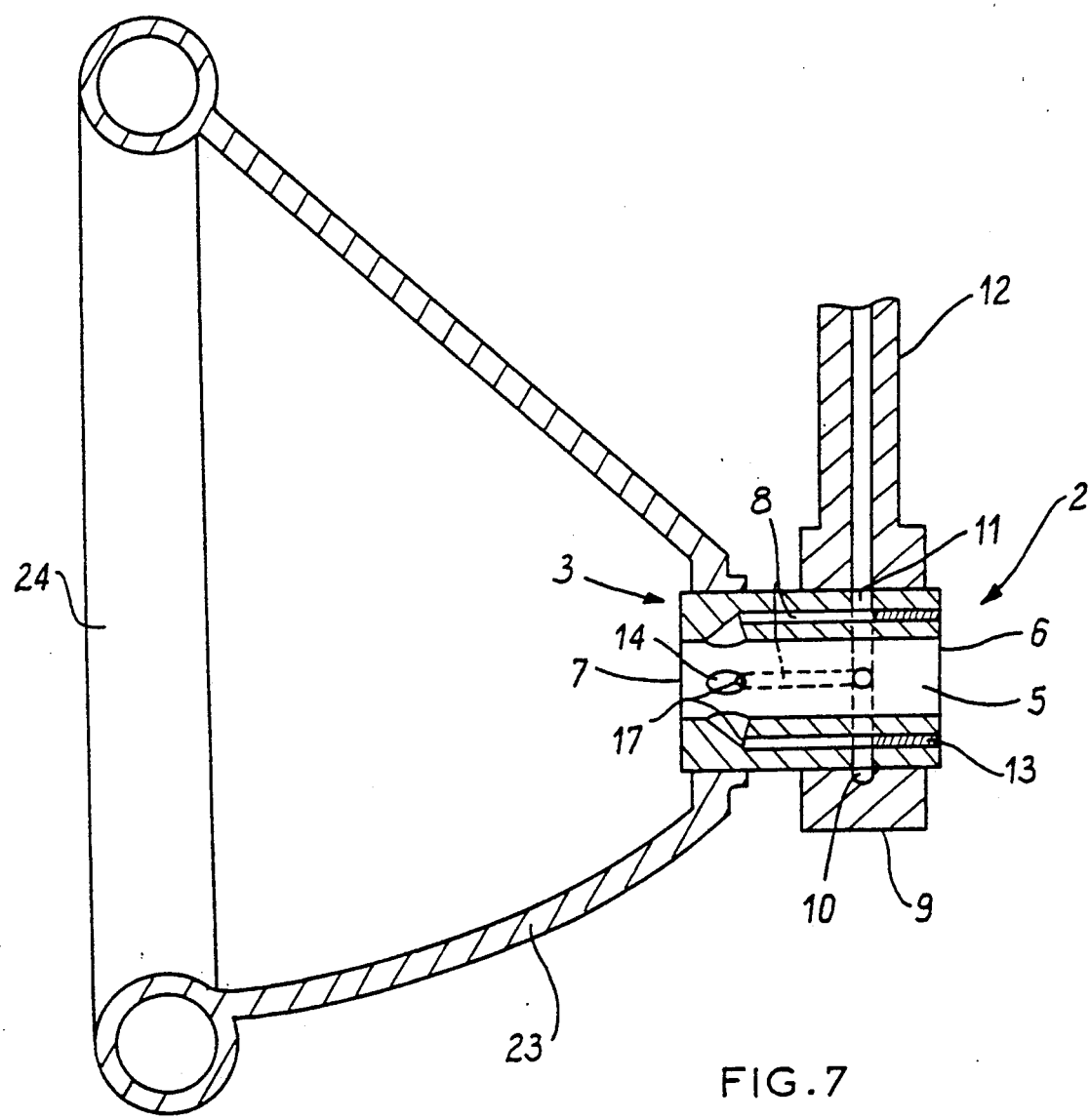
FIG. 7 shows, in axial section, another embodiment of the device of the invention, in which the main tube is no longer intended to be introduced directly into a breathing tract, but forms the end-piece of a breathing aid mask to be applied to the face (mouth and/or nose) of a patient.

The device of FIG. 7 is distinguished from the devices of FIGS. 1 to 6 both by the fact that tube 1 is not intended to be introduced directly into a breathing tract but forms the end-piece of a mask and by the fact that the dimensions (length, diameters) are different. According to FIG. 7, the main tube forms the air inlet and outlet end-piece for a mask which, in addition, is of known type, namely comprising essentially a shell 23, a sealing pad 24 and fixing means (not shown) such a straps.

FIG. 7 also illustrates a variant of recess 14, the deflection means here not forming a continuous annular groove, but being formed of a discontinuous assembly of generally conical shaped recesses, formed in wall 15 and at the bottom of each of which opens the distal end of an auxiliary channel 8.

The operating principle of the device of FIG. 7 is of course the one described above in connection with FIGS. 1 to 6.

Furthermore, although FIG. 7 comprises a tube in which the breathing system only acts in the breathing in direction (as in the case of the device of FIG. 1), a mask may also be equipped with a device according to FIG. 6, for breathing in and breathing out systems.

Tube 4 forming part of the embodiments of the device of the invention may be made from any material already used in breathing probes, for example from polyvinyl chloride, with a silicon coating if required or from steel permitting high pressure injections.

Of course, the dimensions of the device of the invention may be very variable, depending essentially on the tract in which the tube is placed and on the size of the patient, who may be an adult, child, infant or a premature baby.

What is claimed is:

1. Breathing aid device comprising a tube having a distal and proximal end and a main channel therebetween, said distal end located in a patient's breathing tract and connecting said patient's breathing tract to the ambient atmosphere or to a pressurized breathable gas source, said device further comprising at least one auxiliary channel formed in a wall of said tube and having a distal orifice opening into said main channel close to the distal end of said tube for injecting a gas jet to ventilate said patient, said auxiliary channel being substantially parallel to said main channel, a first face and a second face formed in the wall of said tube, said distal orifice being located in said first face, said first face diverging from the center axis of said main channel towards the auxiliary channel, said second face being opposite said first face and converging towards the center axis of said main channel in the direction of the distal end of said tube, said second face forming a means to deflect said gas jet towards the center of said main channel.

2. Device according to claim 1, wherein said device includes several auxiliary channels formed in the wall of said tube, and wherein the distal orifices of said auxiliary channels are formed in said first face.

3. Device according to claim 2, characterized in that said second face is extended towards said distal end of said tube by a wall, said wall serving to slightly widen said main channel.

4. Device according to claim 3, wherein said deflection means are formed in an end-piece, said end-piece being afixable to the distal end of said tube.

5. Device according to claim 1, characterized in that said deflection means are formed of a discontinuous assembly of recesses, each of said recesses having a generally conical shape, said assembly of recesses being formed in the internal wall of said tube, the bottom of each of said recesses forming in opening for the distal end of an auxiliary channel.

6. Device according to claim 1, characterized in that it comprises a plurality of auxiliary channels, at least some of said channels being supplied by a common source of pressurized breathing gas.

7. Device according to claim 6, characterized in that the common supply of said channels is provided via a distribution ring coaxial with said tube.

8. Device according to 5 or 6, characterized in that said auxiliary channels which are not supplied by a common source serve for introducing additional gas products, such as medical products or humid gases.

9. Device according to claim 1, characterized in that said device comprises at least one additional auxiliary channel, independent of said auxiliary channel and connected to a pressurized gas source, each of said at least one additional auxiliary channels opening into said main channel close to the proximal end of said main channel and at least the proximal end of each of said at least one additional auxiliary channels being parallel to said main channel, and each of said at least one additional auxiliary channels further including means for deflecting the gas jet passing through said at least one additional auxiliary channel in the direction of the axis of said main channel, said deflection means being disposed opposite the opening in said at least one additional auxiliary channel which is close to the proximal end of said main channel.

10. Device according to claim 9, characterized in that said auxiliary channels and said deflection means are arranged similarly in the proximal and distal portions of said device.

11. Device according to claim 1, characterized in that said device forms an air inlet and outlet end-piece for a breathing aid mask, said breathing aid mask intended to be applied to the face of a patient.

12. Breathing aid mask, characterized in that said breathing aid mask is provided with a breathing aid according to claim 11.

* * * * *